US006423877B1

(12) United States Patent
Corey

(10) Patent No.: US 6,423,877 B1
(45) Date of Patent: Jul. 23, 2002

(54) SYNTHESIS OF PSEUDOPTEROSIN COMPOUNDS

(75) Inventor: Elias J. Corey, Cambridge, MA (US)

(73) Assignee: President and Fellows of Harvard College, Cambridge, MA (US)

(*) Notice: Subject to any disclaimer, the term of this patent is extended or adjusted under 35 U.S.C. 154(b) by 0 days.

(21) Appl. No.: 09/712,884

(22) Filed: Nov. 15, 2000

Related U.S. Application Data
(60) Provisional application No. 60/165,603, filed on Nov. 15, 1999.

(51) Int. Cl.$^7$ .............................................. C07C 37/00
(52) U.S. Cl. ........................ 568/771; 568/733; 435/135
(58) Field of Search ................................. 585/430, 435, 585/440; 568/374, 376, 506, 733, 771; 435/135

(56) References Cited

PUBLICATIONS

E. J. Corey et al, "A Direct and Efficient Stereocontrolled Synthetic Route to the Psedopterosins, Potent Marine Antiinflammatory Agents", J. Am. Chem. Soc., vol. 120 (1998), pp 12,777–12,782.*

Samuel Danishefsky et al, "The Reaction of Enamines with Activated Butadienes, A One–Step synthesis of Benzenes", J. Org. Chem., vol. 30 (1965), pp 3676–3679.*

John C. Leffingwell et al, "A New Synthetic Method for the Preparation of Aromatic Aldehydes, Ketones, and Schiff Bases", J. Chem. Soc., Chem. Comm., (1969), pp 1151–1152.*

Miloš Hudlický, "Oxidations in Organic Chemistry", ACS Monograph 186, Amer. Chem. Soc., (1990), pp 32–33.*

Fenical, "Marine Soft Corals of the Genus Pseudopterogorgia: A Resource for Novel Anti–Inflammatory Diterpenoids", *Journal of Natural Products*, vol. 50, No. 6, pp. 1001–1008, Nov.–Dec. 1987.

Look et. al., "The Seco–Pseudopterosins, New Anti–Inflammatory Diterpene–Glycosides From a Caribbean Gorgonian Octocoral of the Genus Pseudopterogorgia", *Tetrahedron*, vol. 43, No. 15, pp. 3363–3370, 1987.

McCombie et. al., "Controlling Benzylic and Anomeric Functionality and Stereochemistry: Methodology and Syntheses Utilising Intramolecular Ionic Hydrogenation", Schering–Plough Research Institute *Synlett*, 8–93, pp. 541–547.

Look et. al., "The Pseudopterosins: A New Class of Antiinflammatory and Analgesic Diterpene Pentosides from the Marine Sea Whip *Pseudopterogorgia elisabethae* (Octocorallia)", *J. Org. Chem.* 1986, 51, 5140–5145.

(List continued on next page.)

Primary Examiner—Johann Richter
Assistant Examiner—Paul A. Zucker
(74) Attorney, Agent, or Firm—Ernest V. Linek; Banner & Witcoff, Ltd.

(57) ABSTRACT

The present invention is directed to a new synthetic route to pseudopterosin aglycone (3):

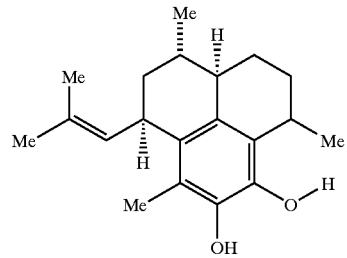

a key intermediate for the synthesis of a group of antiinflammatory natural products including pseudopterosin A (1) and E (2). The pathway of synthesis starts with the abundant and inexpensive (S)-(–)-limonene and its long-known cyclic hydroboration product (4) and leads to the chiral hydroxy ketone (6). Conversion of (6) to (10) followed by a novel aromatic annulation produced (15) which underwent highly diastereoselective cyclization to afford the protected pseudopterosin aglycone (16). The naturally occurring pseudopterosins such as (1) and (2) are readily available from this key intermediate.

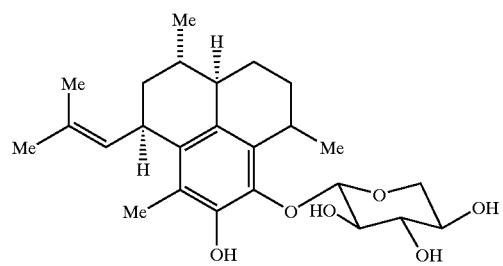

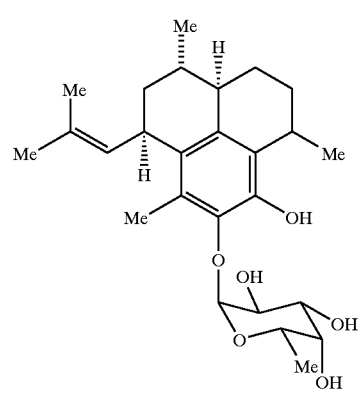

5 Claims, No Drawings

OTHER PUBLICATIONS

Ranu et. al., "Surface–mediated Solid Phase Reaction. Part 6.[1] Mukaiyama–Michael Addition of Silyl Enol Ethers to Alkyl Vinyl Ketones on the Surface of Alumina: a Simple and Convenient Method for the Synthesis of 1,5–Diketones", *J. Chem. Soc. Perkin Trans.* 1 1994.

Brown et. al., "Thexylborane as a Convenient Reagent for the Cyclic Hydroboration of Dienes. Stereospecific Syntheses via Hydroboration", *J. Am. Chem. Soc. 89*:21 10–11–67.

Heathcock et. al., "Steroeselection in the Michael Addition Reaction. 1. The Mukaiyama–Michael Reaction[1]", *J. Am. Chem. Soc. 1985*, 107, 2797–2799.

Look et. al., "The pseudopterosins: Anti–inflammatory and analgesic natural products from the sea whip *Pseudopterogorgia elisabethae*" *Proc. Natl. Acad. Sci. USA* vol. 83, pp. 6238–6240, Sep. 1986 Chemistry.

Corey et. al., "Optical Rotation and Helical Polypeptide Chain Configuration in $_a$–Proteins", *J. Am. Chem. Soc.* vol. 79 pp. 248 1957.

Gill et. al., "A synthetic approach to the pseudopterosins", *Chem. Commun.*, 1996 pp 1743–1744.

LeBrazidec et. al., "Synthetic approaches to pseudopterosin G aglycone dimethyl ether", *J. Chem. Soc., Perkin Trans. 1*, 1998.

Narasaka et. al., "The Michael Reaction of Silyl Enol Ethers with a, β–Unsaturated Ketones and Acetals in the Presence of Titanium Tetraalkoxide and Titanium Tetrachloride", *Bulletin of the Chem. Soc. of Japan*, vol. 49(3), 779–783 (1976).

Corey et. al., "The Application of a Mechanistic Model Leads to the Extension of the Sharpless Asymmetric Dihydroxylation to Allylic 4–Methoxybenzoates and Conformationally Related Amine and Homoallylic Alcohol Derivatives", *J. Am. Chem. Soc.* 1995, 117, 10805–10816.

Deslongchamps et. al., "The total synthesis of (+)–ryanodol. Part II. Model studies for rings B and C of (+)–anhydroryanodol. Preparation of a key pentacyclic intermediate", *Can. J. Chem.* vol. 68, 1990.

Sodeoka et. al., "Highly Efficient Synthesis of Carbacyclin Analogue. Stereospecific Synthesis of Aryl–Substituted Exocyclic Olefin", *J. Am. Chem. Soc.* 1988, 110, 4823–4824.

Corey et. al., "Enantiospecific Total Synthesis of Pseudopterosins A and E", *J. Am. Chem. Soc.* 1989, 111, 5472–5474.

Vedeja et. al., "An E–Selective 1,3–Diene Synthesis from Moderated Ylides and Aldehydes", *J. Org. Chem.* 1984, 49, 210–212.

Broka et. al., "Total Synthesis of (–)–Pseudopterosin A" *J. Org. Chem.* 1988, 53, 1584–1586.

Anelli et. al., "Oxidation of Diols with Alkali Hypochlorites Catalyzed by Oxammonium Salts under Two–Phase Conditions" *J. Org.Chem.* 1989, 54, 2970–2972.

Brown et. al., "Boraheterocycles Via Cyclic Hydroboration", *Tetrahedron* vol. 33, pp. 2331–2357.

Corey et. al., "A New Enantiospecific Route to The Pseudopterosins", *Tetrahedron Letters*, vol. 31, No. 27, pp. 3857–3858, 1990.

Stevens et. al., "Further Studies on the Utility of Sodium Hypochlorite in Organic Synthesis. Selective Oxidation of Diols and Direct Conversion of Aldehydes to Esters", *Tetrahedron Letters*, vol. 23, No. 45, pp. 4647–4650, 1982.

McCombie et. al., "Controlling Benzylic Functionality and Steroechemistry: 1. Synthesis of the Secopseudopterosin Aglycone", *Tetrahedron Letters*, vol. 32, No. 19, pp. 2083–2086. 1991.

Majdalani et. al., "Chiral $\eta^6$–Arene–Cr(CO)$_3$ Complexes in Organic Synthesis: A Short and Highly Selective Synthesis of the 18–nor–seco–Pseudopterosin Aglycone", *Tetrahedron Letters* vol. 38, No. 26, pp. 4545–4548, 1997.

Majdalani et. al., "Enantioselective Synthesis of the Aglycones of Pseudopterosin and seco–Pseudopterosin via a Common Synthetic Intermediate", *Synlett.* 1997 pp. 1303–1305.

Terao et. al., "A Facile Synthesis of Allylic Alcohols", *Synthesis* 1979 pp. 467–468.

Cristau et. al., "Synthesis of Diphenyldialkylphosphonium Salts", *Synthesis* 1988 pp. 911–912.

Buszek et. al., "Total Synthesis of Pseudopterosin A and E Aglycon", *Tetrahedron Letters* vol. 36, No. 50, pp. pp. 9129–9132, 1995.

Buszek, "First Intramolecular Benzyne Diels–Alder Reaction with an Acyclic Diene. Unusual Effect of Diene Geometry on the Course of the Reaction", *Tetrahedron Letters*, vol. 36, No. 50, pp. 9125–9128, 1995.

Rouhi, "Supply Issues Complicate Trek of Chemicals From Sea to Market", *Chem. Eng. News*, Nov. 20, pp. 42–44.

Mashraqui et. al., "Active MnO$_2$. Oxidative Dehydrogenations", *Synth. Commun.* 1982, vol. 12, pp. 637–645.

\* cited by examiner

SYNTHESIS OF PSEUDOPTEROSIN COMPOUNDS

CROSS-REFERENCE TO RELATED APPLICATION

This application claims priority under 35 U.S.C. §119 of commonly owned Provisional Application Serial No. 60/165,603, filed Nov. 15, 1999, the disclosure of which is hereby incorporated herein by reference.

STATEMENT OF GOVERNMENT SUPPORT

This invention was supported in part by funding received from the National Science Foundation, Grant No. CHE9300276 and from the National Institutes of Health, Grant No. GM34167. Thus, the Government of the United States has certain rights in this invention.

BACKGROUND OF THE INVENTION

The pseudopterosins are compounds produced by the Caribbean sea whip *Pseudopteragoria elisabethae*. These compounds are exemplified by the structures shown below, pseudopterosin A (Compound 1) and E (Compound 2),[1] which are remarkably active antiinflammatory agents[2] that were discovered by W. Fenical and collaborators.

The analgesic activity of Compound 1 (administered subcutaneously) is several fold greater than that of indomethacin,[2] and that of Compound 2 is some 50 times greater.[3] This potency and the fact that the biological mode of action of Compounds 1 and 2 appears to be novel[2] have made these substances (and their analogues) attractive targets for synthetic and for biological/biochemical research.

Further interest in the pseudopterosins derives from their commercial use as topical antiinflammatory agents in the cosmetic field and the limited supply available from natural sources.[4] A number of laboratories have described studies on the total synthesis of pseudopterosins. The earliest syntheses were developed by C. A. Broka and co-workers[5] and in these laboratories,[6] including the first sterocontrolled enantioselective syntheses of Compounds 1 and 2 from either (+)-menthol$_{6a}$ or (S)-citronellal.[6b] Subsequently, a variety of additional synthetic approaches have been developed b other groups.[7-10] Although the more recent syntheses involve fascinating and elegant design, they appear to fall short of practicality.

SUMMARY OF THE INVENTION

One preferred embodiment of the present invention is a new synthetic route to pseudopterosin aglycone (3):

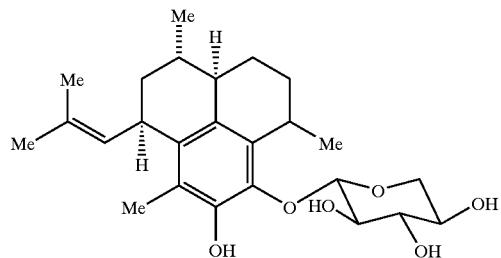

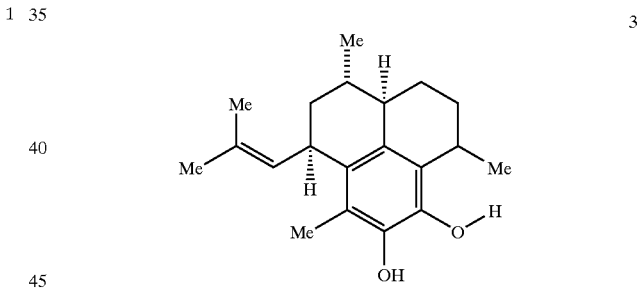

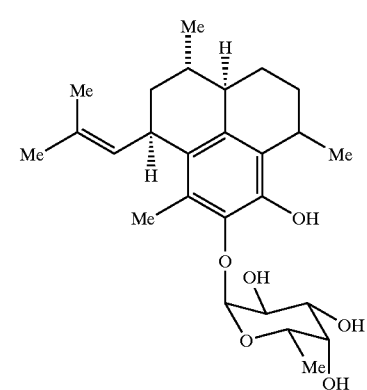

an intermediate for the synthesis of a group of antiinflammatory natural products including pseudopterosin A (Compound 1) and E (Compound 2).

The synthetic pathway of the present invention is outlined below in Scheme I, and starts with the abundant and inexpensive (S)-(−)-limonene and its long-known cyclic hydroboration product (Compound 4) and leads to the chiral hydroxy ketone (Compound 6). Conversion of Compound 6 to Compound 10, followed by a novel aromatic annulation produced Compound 15 which underwent highly diasterioselective cyclization to afford the protected pseudopterosin aglycone (Compound 16). The naturally occurring pseudopterosins such as (Compound 1) and (Compound 2) are readily available from this intermediate. This intermediate will also serve as a source of novel synthetic pseudopterosin compounds.

Scheme 1:

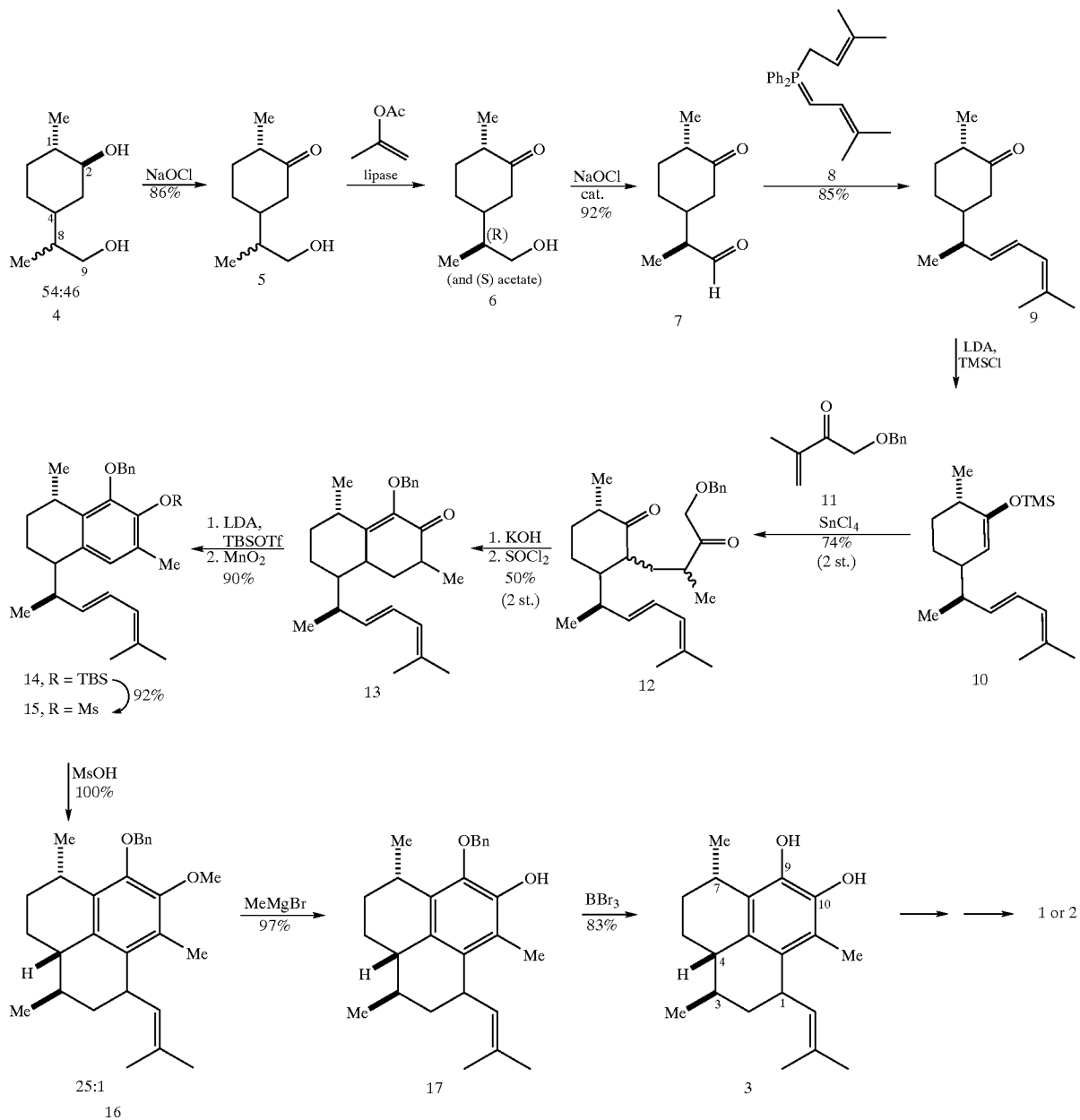

Thus, one preferred embodiment of the present invention is a new process for the synthesis of pseudopterosin compounds which has a number of advantages over previously known methods; including (1) an inexpensive chiral starting material (limonene), (2) the use of common or readily available reagents, (3) stereocontrol, (4) simplicity of execution, (5) good yields, and (6) directness. In addition, this synthesis illustrates a number of new and potentially widely useful synthetic methods of noteworthy aspects of stereocontrol and site selectivity.

The present invention is thus directed to the synthetic process outlined in Scheme 1, to the novel intermediates obtained therein, and to the uses of these compounds as synthetic precursors to the pseudopterosins. Other embodiments and aspects of the present invention include the novel synthetic procedures described herein, as detailed below.

DETAILED DESCRIPTION OF THE INVENTION

As described above, the starting material for the present synthesis of pseudopterosin compounds was diol mixture (4) which can be obtained in nearly quantitative yield from (S)-(−)-limonene by cyclic hydroboration and alkaline peroxide oxidation.[11] Although this mixture of diols (nearly 1:1) is readily available in quantity, it is believed that this mixture has neither been separated nor been used as starting material in a stereocontrolled synthesis. Neither distillation nor chromatographic methods allow separation of the mixture. Nonetheless, it has been found that the diastereomeric mixture can be utilized for synthesis using the novel separation process, as outlined above in Scheme 1.

Referring to Scheme 1, the process of the present invention was started by subjecting a nearly 1 to 1 diastereomeric mixture of diols (4) (54:46 C(8)) to selective oxidation at C(2) upon exposure to 1.5 equiv of sodium hypochlorite[12] in aqueous acetic acid. This formed the diastereomeric mixture of hydroxy ketones 5 in excellent yield. Exposure of this hydroxy ketone mixture to isopropenyl acetate in isopropyl ether at 23° C. using Amano PS lipase as the catalyst resulted in selective acetylation of the (8S)-hydroxy ketone after 17 h. Flash chromatography of the resulting mixture on silica gel afforded the desired (8R)-alcohol 6 (36% based on 5) as an oil (ratio 8R/8S=99:1 as determined by HPLC analysis of the corresponding p-nitrobenzoate ester) and the acetate of the (8S)-diastereomer of 6. Oxidation of 6 in a $CH_2Cl_2$—$H_2O$ system with sodium hypochlorite and 2,2,6,6-tetramethyl-1-piperidinyloxy radical (TEMPO) as catalyst[13] at pH 8 gave keto aldehyde 7 in 92% yield. Wittig-Vedejs E-selective olefination[14a] of 7 using the ylide 8[14b] as reagent in dimethozyethane produced the E-diene 9 in excellent yield, as shown in Scheme 1, without the loss of stereochemical integrity at the labile C(8) position.

With the successful establishment of three of the four stereocenters of pseudopterosin aglycone (3), the next task called for in the synthetic plan was the attachment of the aromatic ring, i.e., the conversion 9–14 in Scheme 1. This was accomplished using a new aromatic annulation protocol starting with Mukaiyama-type Michael coupling of the enol silyl ether 10 and the functionalized α,β-enone 11.[15,16] This coupling product was obtained in 74% yield (correcting for a small amount of recovered 9) using 1.1 equiv of $SnCl_4$ as the catalyst in $CH_2Cl_2$ at −78° C. of 40 min. Treatment of Compound 12 with ethanolic KOH at 0° C. effected aldol cyclizaton to a β-hydroxy ketone which was dhydrated by treatment with $SOCl_2$-pyridine at 23° C. for 1 h to form the α,β-enone 13. The enol tert-butyldimethylsiyl (TBS) either of Compound 13 was prepared by deprotonation (alpha to methyl) and silylation with TBS-triflate, and then the resulting ether was aromatized by stirring with activated $MnO_2$ (Aldrich Co., Milwaukee) in methylcyclohexane at 70° C. for 36 h to provide the aromatic hydronaphthalene 14 in 90% overall yield from 13.

It was found that the $MnO_2$-induced aromatization process proceeds more readily and in higher yield with methylcyclohexane as solvent than in benzene or toluene as solvent[17] and that by using the dry $MnO_2$-methylcyclohexane system aromatization of a wide range of Compound 1,4- and 1,3-cyclohexadienes can be effected efficiently. A summary of these studies is presented below. In contrast to the success achieved using the $MnO_2$-methylcyclohexane aromatization system, a number of other oxidants that have previously been recommended for aromatization failed, including (q) Pd-X, (2)dichlorodicyanoquinone, (3) o-chloranil, (4) 2,6-dichloro-1,4-benzoquinone, and (5) $Cr(CO)_3·3CH_3CN$, norbornene.[18]

Desilylation of Compound 14 ($Bu_4NF$ in THF) and reaction with $CH_3$—$SO_2Cl$—$Et_3N$ in $CH_2Cl_2$ provided the mesylate 15 which upon treatment with 5 equiv of $CH3SO3H$ in $CH_2Cl_2$ at −50° C. underwent highly diasteroselective cationic cyclization (25:1) to form 16 in very high yield. Reaction of Compound 16 with MeMgBr produced cleanly the monophenol 17 which was debenzylated to give pseudopterosin aglycone (3). The various pseudopterosins may be accessed from 17 or 3 by procedures previously developed in these laboratories.[6] Comparison of synthetic 3 $[\alpha]^{23}_D$−95 (c=1, $CHCl_3$) with authentic 3[6] revealed identical IR, $^1H$ NMR, $^{13}C$ NMR, and high-resolution mass spectra.

It is interesting that the methanesulfonic acid cyclization of TBS ether 14 afforded primarily (8:1) the product 18, corresponding to 16 with the (S)-configuration at C(1). This remarkable difference in the sterochemistry of cationic cyclization of Compound 14 and 15, clearly dependent on the electron-donating properties of TBSO vs. MsO, is most readily explained as due to a difference in mechanistic pathway, as shown in Scheme 2.

Scheme 2:

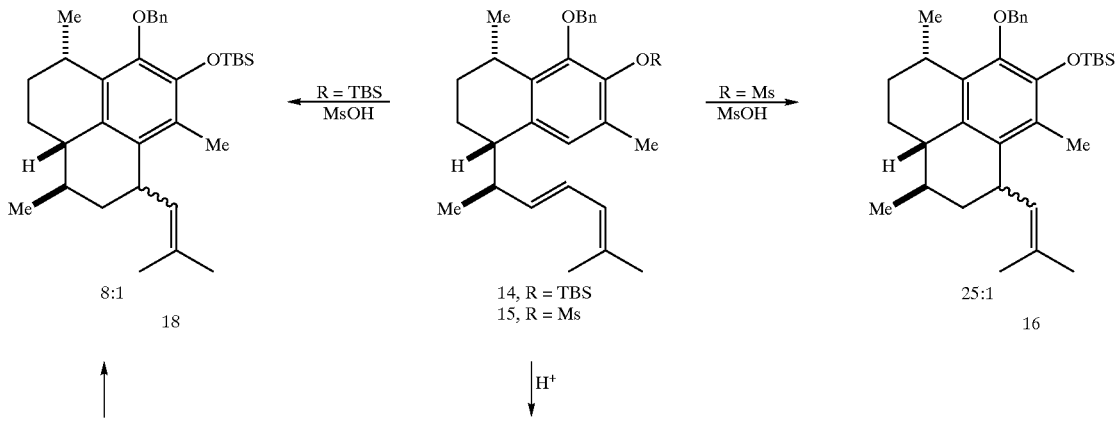

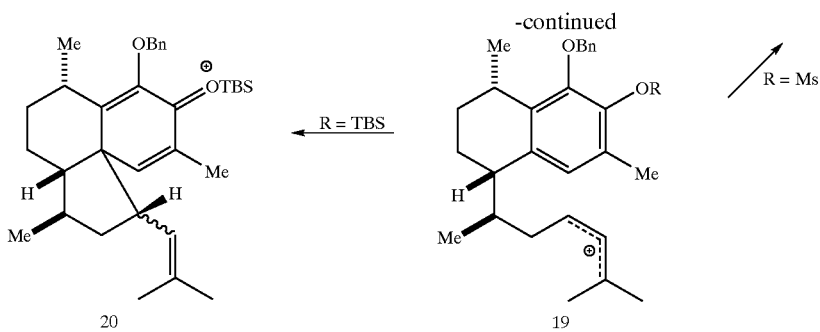

The pathway from 15 to 16 probably involves direct 6-membered ring closure of allylic cation 19. However, as shown above in Scheme 2, the pathway from 14 to 18 can most reasonably be explained by cyclization of allylic cation 19 to the 5-membered spiro cation 20[19] followed by 1,2-rearrangement with 5→6 ring expansion. Thus, the differences in stereopreferences for formation of Compound 16 and 18 reflect stereoelectronic preferences of the intermediate steps 19→16 and 19→20.

It is believed that the synthetic process described herein and outlined in Scheme 1 provides a very direct and practical route for the synthesis of pseudopterosin compounds in quantity. In addition, a number of the steps illustrated in Scheme 1 are also of broader interest from the viewpoint of general synthetic methodology, including (1) the use of an inexpensive, recoverable lipase to effect separation of the diastereomers of 5, (2) the new procedure for the aromatic annulation of 9→14, (3) the remarkably stereoselective cyclizations of Compound 15→16 and 14→18, and (4) the superiority of $MnO_2$ as a mild reagent for aromatization of cyclohexadienes. Accordingly, these steps are considered to be particularly preferred embodiments of the present invention.

With regard to the usefulness of dry $MnO_2$ in methylcyclohexane as a reagent for the aromatization of cyclohexadienes, presented below are additional results that have been obtained with a diverse collection of substrates, as summarized in Table 1. The aromatization reactions, which were generally monitored by thin-layer chromatography, proceed at varying rates as shown in Table 1. The aromatization of dimethyl trans-1,2 dihydrophtyhalate was found to be considerably faster than that of various alkyl- or oxy-substituted dihydrobenzenes, an indication that the first step in the process may be a hydrogen atom rather than a hydride abstraction.

TABLE 1

Aromatization of Cyclohexadienes by $MnO_2$ at 70° C. in Methylcyclohexane

| Substrate | Product | Time (yield) |
|---|---|---|
| 21 | 22 | 36 h (84%) |
|  |  | 5 h (80%) |
|  |  | 18 h (73%) |
|  |  | 16 h (43%)[a] |

TABLE 1-continued

Aromatization of Cyclohexadienes by
MnO₂ at 70° C. in Methylcyclohexane

| Substrate | Product | Time (yield) |
|---|---|---|
| 23 | 24 | 36 h (83%) |
| 25 | 26 | 36 h (82%) |

[a] Low yield due to volatility of product.
[b] An = 4-methoxyphenyl.

The present invention will be further illustrated with reference to the following examples which aid in the understanding of the present invention, but which are not to be construed as limitations thereof. All percentages reported herein, unless otherwise specified, are percent by weight. All temperatures are expressed in degrees Celsius.

EXAMPLE 1

(1S, 4S, 8R,S)-Menth-2-one-9-ol (5)

A solution of a 54:46 mixture of C(8) diastereomeric diols 4 (7.225 g, 41.94 mmol) in acetic acid (70 mL) was treated with aqueous sodium hypochlorite (33.1 mL, 63 mmol) dropwise over 15 min.[12] The mixture was stirred at 23° C. for 4 h. Isopropyl alcohol (10 mL) was added, and the mixture was stirred an additional 10 min. After the mixture was concentrated in vacuo to remove most of the acetic acid, water was added, and the aqueous solution was extracted three times with $CH_2Cl_2$. The organic layers were carefully washed with $NaHCO_3$ (saturated aqueous), and the $NaHCO_3$ was extracted twice with $CH_2Cl_2$. The organic layers were carefully washed with $NaHCO_3$ (saturated aqueous), and the $NaHCO_3$ was extracted twice with $CH_2Cl_2$. The combined organic layers were dried over $MgSO_4$ and concentrated in vacuo. Flash chromatography ($CH_2Cl_2$-EtOAc 90:10–75:25) afforded 6.11 g (86%) of hydroxy ketone 5 as a clear oil with a diastereomeric ratio of 54:46 (determined by HPLC analysis of the p-nitrobenzoate ester): $R_f$=0.26 (hexanes-EtOAc, 5:50); $^1H$ NMR (400 MHz, $CDCl_3$) δ3.63–3.48 (m, 2H), 2.39–2.34 (m, 2H), 2.19–2.07 (m, 2H), 1.88–1.82 (m, 2H), 1.70–1.20 (m, 4H), 1.01 (d, J=6.5 Hz, 3H), 0.93 (m, 3H).

EXAMPLE 2

(1S, 4S, 8R)-(+)-Menth-2-one-9-ol (6)

The above mixture of keto alcohols 5 (3.89 g, 22.85 mmol) in isopropyl ether (175 mL) was treated with amano PS lipase (1.13 g) followed by isopropenyl acetate (5.0 mL, 45.70 mmol) and stirred at 23° C. The progress of the reaction was monitored by NMR analysis of small aliquots. After 17 h, the reaction mixture was filtered and concentrated. Flash chromatography (using as eluent hexanes-$Et_2O$ 70:30, followed by $Et_2O$) afforded acetylated product and 1.412 g (36%) of the desired keto alcohol 6 as an oil of 98% de (determined by HPLC analysis of the p-(nitrobenzoate ester): $R_f$=0.26 (hexanes-EtOAc 50:50); $[\alpha]^{23}_D$+4.0 (c 0.96, $CHCl_3$); FTIR (film) 3440, 1710 cm$^{-1}$; $^1H$ NMR (400 MHz, $CDCl_3$) δ3.55 (dd, J=10.7, 6.1 Hz, 1H), 3.47 (dd, J=10.7, 6.3 Hz. 1H), 2.35–2.26 (m, 2H), 2.19–2.055 (m, 3H), 1.89–1.78 (m, 2H), 1.56 (sept, J=6.2 Hz, 1H), 1.44 (dq, J=13.0, 3.3 Hz, 1H), 1.27 (dq, J=13.0, 3.3 Hz, 1H), 0.97 (d, J=6.5 Hz, 3H), 0.90 (d, J=6.9 Hz, 3H); $^{13}C$ NMR (100 MHz, $CDCl_3$) δ6 213.5, 65.6, 46.3, 45.0, 41.7, 40.3, 35.0, 27.6, 14.3, 13.2; CIMS ($NH_3$) 188 (M+$NH_4$)$^+$, 170[M]$^+$, 153 [M−OH]$^+$; HRMS calcd for $[C_{10}H_{18}O_2+H]^+$ 171.1389; HPLC (CHIRAL) Chiralpack at 23° C. λ=254 nm, hexane-isopropyl alcohol 85:15, retention times: 25.1 min (major), 33.2 min (minor) at 1 mL/min flow rate.

EXAMPLE 3

(1S, 4S, 9R)-(−)Menthane-2,9-dione (7)

A solution of keto alcohol 6 (0.404 g, 2.37 mmol) in $CH_2Cl_2$ (8 mL) was treated with 2,2,6,6-tetramethyl-1-piperidinyloxy, free radical (TEMPO) (0.008 g, 0.051 mmol) and potassium bromide (0.028 mL, 0.237 mmol).[13] The solution was cooled to 0° C. and treated with 6% aqueous sodium bypochlorite which had been adjusted to pH~8 using $NaHCO_3$ (4.0 mL, 3.8 mmol). The reaction mixture was stirred at 0° C. for 1.5 h and poured into 0.1 M HCl (30 mL). The aqueous solution was extreacted thre times with $CH_2Cl_2$, and the combined organic extracts were washed with $Na_2S_2O_3$ (saturated aqueous). The organic layer was dried over $Na_2SO_4$ (anhydrous), filtered, and concentrated in vacuo. Flash chromatography (hexanes-EtOAc 75:25) afforded 0.367 g (92%) of desired keto aldehyde 7 as a clear oil: $R_f$=0.30 (hexanes-EtOAc 70:30); $[\alpha]^{23}_D$−45.5 (c 1.20, $CHCl_3$); FTIR (film) 1714 cm$^{-1}$; $^1H$ NMR (500 MHz, $CDCl_3$) δ211.5, 203.8, 50.9, 45.9, 44.8, 40.0, 34.5, 27.9. 14.3, 9.8; EIMS 168[M]$^+$; HRMS calcd for $[C_{10}H_{16}O_2]^+$ 168.1150, found 168.1151.

EXAMPLE 4

Keto Diene 9

Diphenyldiprenylphosphonium bromide (0.956 g, 2.37 mmol)[14b] was azeotropically dried with benzene (2×2 mL), dissolved (mostly) in dimethoxyethane (20 mL), cooled to 0° C., and treated with potassium tert-butoxide (2.37 mL, 1 M solution to DME, 2.37 mmol).[14] The mixture immediately turned red. This solution of ylide 8 was transferred dropwise via cannula to a solution to keto aldehyde 7 (0.362 g 2.15 mmol) in DME (20 mL) at −60° C., over 3 min the ylide solution was washed in with an additional 2 mL DME). After 10 min NH$_3$Cl (saturated aqueous) was added, and the reaction mixture was partitioned between water and ether. The organic layer was separated, and the aqueous phase was extracted again with ether. The combined organic layers were washed with brine, dried over MgSO$_4$ (anhydrous), filtered, and concenterated in vacuo. Flash chromatography (hexanes-EtOAc 80:20) afforded 0.401 g (85%) of keto diene 7 as a clear oil: R$_f$=0.66 (Hexanes-EtOAc 70:30); $[\alpha]^{23}{}_D$+7.21 (c 1.04, CHCl$_3$); δ6.18 (dd, J=15.1, 10.8 Hz, 1H) 5.78 (d, J=10.9 Hz, 1H), 5.39 (dd, J=15.1, 8.5 Hz, 1H), 2.41 (ddd, J=13.2, 3.6, 2.3 Hz, 1H), 2.31 (sept, J=6.3 Hz, 1H), 2.16, m, 1H), 2.08 (m, 1H), 2.01 (dt, J–13.2, 0.9 Hz, 1H), 1.86 (m, 1H), 1.76 (s, 3H), 1.74 (s, 3H), 1.66 (m, 1H), (dq, J=12.8, 3.6 Hz, 1H) 1.30 (dq, J=13.1, 3.4 Hz, 1H), 1.02 (d, J=6.8 Hz, 3H), 1.00 (d, J=6.4 Hz, 3H); $^{13}$C NMR (100 MHz, CDCl$_3$) 213.5, 134.2, 133.7, 126.9, 124.9, 45.8, 45.5, 44.9, 42.3, 35.0, 29.5, 25.9, 18.3 17.8, 14.4; CIMS (NH$_3$) 238 [M+NH$_4$]$^+$, 221 [M+H]$^+$; HRMS calcd for [C$_{15}$H$_{24}$O+ NH$_4$]$^+$ 238.2171, found 238.2171.

EXAMPLE 5
Enol Ether 10

A solution of diisopropylamine (0.084 mL, 0.6 mmol) in DME (1 mL) was coolded at 0° C. and treated dropwise with n-BuLi (0.232 mL, 2.59 M in hexanes, 0.6 mmol). The solution was stirred for 15 min, cooled to −78° C., and treated with cholotrimethylsilane (0.152 mL, 1.20 mmol). In a separate flask keto diene 9 (0.0265 mg, 0.120 mmol), was azeotropically dried with benzene (1 mL), dissolved in DME (1 mL), and transferred dropwise via cannula to the reaction mixture (remaining 9 was washed in with an additional 0.5 mL of DME). After 5 min the reation mixture was trated with dry triethylamine (1 mL) and NaHCO$_3$ (saturated aqueous) and warmed to 23° C. The mixture was diluted with water and extracted three times with petroleum ether. The combined organic layers were dried over K$_2$CO$_3$ (anhydrous), filtered,and concentrated in vacuo. This afforded 0.0359 g (100%) of enol ether 10 as an 8:1 mixture of regioisomers (as determined by $^1$H NMR analysis): R$_f$=0.68 (hexanes-EtOAc-Et$_3$N, 89;10:1); $^1$H NMR (400 MHz, C$_6$D$_6$) δ6.35 (dd, J=15.0, 10.8 Hz, 1H), 5.94 (d, J=10.1 Hz, 1H) 5.53 (dd, J=15.1, 8.4 Hz, 1H), 5.00 (s, 1H), 2.2–1.9 (m, 3H), 1.80 (m, 1H), 1.6 (a, 2H), 1.65 (s, 3H), 1.63 (m, 1H), 1.3–1.1 (m, 2H), 1.16 (d, J=6.8 Hz, 3H), 1.04 (d, J=6.7 Hz, 3H), 0.21 (s, 9H).

EXAMPLE 6
α,βEnone 11

A solution of oxalyl chloride (0.523 mL, 6.00 mmol) in CH$_2$Cl$_2$ (3 mL) was cooled to −78° C. and treated dropwise with DMSO (0.929 mL, 13.1 mmol) in CH$_2$Cl$_2$ (4 mL). After 10 min, the reaction mixture (at −78° C.) was treated dropwise with a solution of Compound 1-benzyloxy-3-methylbut-3-ene-2-ol[15] (azeotroped with 2 mL of benzene, 1.049 g, 5.46 mmol) in CH$_2$Cl$_2$ (4 mL) The reaction mixture was stirred for 15 min and treated dropwise with diisopropylethylamine (4.76 mL, 27.3 mmol). After 15 min, the solution was warmed to 23° C. Water was added, and the organic layer was separated. The aqueous layer was extracted again with CH$_2$Cl$_2$, and the combined organic layers were dried over Na$_2$SO$_4$ (anhydrous), filtered, and concentrated. Flash chromatography (hexanes-EtOAc 90:0) afforded 0.941 g (91%) of enone 11 as a clear oil: R$_f$=0.38 (hexanes-EtOAc 75:25); FTIR (film) 1693 cm$^{-1}$; $^1$H NMR (400 MHz, CDCl$_3$) δ7.37–7.32 (m, 5H), 5.90 (s, 1H), 5.79 (q, J=1.5 Hz, 1H), 4.62 (s, 2H), 4.50 (s, 2H), 1.90 (dd, J=1.5, 1.0 Hz, 3H); $^{13}$C NMR (100 MHz, CDCl$_3$) δ197.6, 142.5, 137.4, 128.5, 128.0, 127.9, 124.9, 73.2, 71.7, 17.5; CIMS (NH$_3$) 208 [M+NH$_4$]$^+$ 208.1338, found 208.1329.

EXAMPLE 7
Diketone 12

Enol ether 10 and enone 11 (0.025 g, 0.132 mmol) were combined, ezeotropically dried with benzene (2×0.5 mL), and dissolved in CH$_2$Cl$_2$ (1.2 mL). The solution was cooled to −78° C. and treated with tin tetrachloride (0.015 mL, 0.132 mmol). After 40 min the reaction mixture was trated with potassium carbonate (1 mL, 5% aqueous solution and warmed to 23° C. The mixture was partitioned between water and extracted twice with CH$_2$Cl$_2$. The organic layer was separated, and the aqueous layer was extracted twice with CH$_2$Cl$_2$. The combined organic layers were washed with water and brine, dried over Na$_2$SO$_4$ (anhydrous), and concentrated in vacuo. Flash chromatography (hexanes-ether 90:10) afforded 0.0058 g (22%) of the starting keto diene 9 and (hexanes-ether 80:20) 0.284 g (58%, 74% with respect to recovered 9) of the Michael adduct 12 as a clear oil: R$_f$=0.52 and 0.58 (hexanes-EtOAc 70:30); FTIR (film) 1708 cm$^{-1}$; $^1$H NMR (of the lower R$_f$) (400 MHz, CDCl$_3$δ7.40–7.29 (m, 5H), 6.20 (dd, J=15,2, 10.7 Hz, 1H), 5.78 (d, J=17.5 Hz, 1H) 4.20 (d, J=10.8 Hz, 1H) 5.48 (dd, J=15.2, 6.9 Hz, 1H), 1.74 (m, 6H), 2.53 (m, 1H), 2.36 (m, 2H), 2.07 (m, 2 H), 2.07 (m, 1H), 1.91 (m, 1H), 1.74 (m, 6H), 1.60–1.07 (m, 5H), 0.95 (m, 9H); EIMS 410[M]$^+$, 392 [M–H$_2$O]$^+$; HRMS calcd for [C$_{27}$H$_{38}$O$_3$]$^+$ 410.2811, found 410.2813.

EXAMPLE 8
α,β-Enone 13

A solution of diketone 12 (0.214 g, 0.521) in ethanol (104 mL) was cooled to 0° C. and treated with potassium hydroxide (0.78 mL, 2 M solution in ethanol, 1.56 mmol). After 1 h, the reaction mixture was treated with pH 4 buffer (100 mL), resulting in a white precipitate. The mixutre was concentrated in vacuo to remove most of the ethanol and extracted three times with ether. The combined organic layers were washed with brine, dried over MgSO$_4$ (anhydrous), filtered, and concentrated. Flash chromatography (hexanes-ether 90:10) afforded 0.150 g (70%) of aldol cyclization product (β-hydroxy ketone) as a white solid: R$_f$=0.27 (hexanes-ether 80:20); $[\alpha]^{23}{}_D$−47 (c 0.86, CHCl$_3$); FTIR (film) 3500, 1726 cm$^{-1}$; $^1$H NMR (400 MHz, CDCl$_3$) δ7.52–7.28 (m, 5H), 6.17 (dd, J=15.2, 6.4 Hz, 1H), 4.78 (d, J=10.5 Hz, 1H), 4.38 (d, J=10.5 Hz, 1H), 3.85 (s, 1H), 2.51 (m, 1H), 2.3 (m, 1H), 2.30 (s, 1H), 2.01 (m, 1H), 1.75 (s, 3H), 1.74 (s, 3H), 1.69–1.20 (m, 8H), 1.10 (d, J=6.4 Hz, 3H), 1.03 (d, J=6.6 Hz, 3H), 0.91 (d, J=7.0 Hz, 3H): $^{13}$C NMR (100 MHz, CDCl$_3$) δ209.1, 137.5, 137.0, 133.1, 128.6, 127.9, 125.5, 125.2, 88.1, 80.8, 72.6, 45.8, 43.4, 42.3, 40.4, 35.7, 34.2, 32.3, 26.0, 25.3, 18.6, 18.3, 14.0, 11.7; CIMS (NH$_3$) 428 [M+NH$_4$]$^+$; HRMS calcd for [C$_{27}$H$_{38}$O$_3$+NH$_4$]$^+$; HRMS calcd for [C$_{27}$H$_{38}$O$_3$+NH$_4$]$^+$ 428.3165, found 428.3157.

A solution of the aboveβ-hydroxy ketone (0.150 g, 0.365 mmol) in pyridine (20 mL0 was treatedwith thionyl chloride (0.107 mL, 1.46 mmol) and stirred at 23° C. After 1.5 h the solution was poured into ice-water and extracted three times with EtOAc. The combined organic layers were washed with brine, dried over Na$_2$SO$_4$ (anhydrous), filtered, and concentrated. Flash chromatography (hexanes-ether 95:5) afforded 0.100 g (70%) of α, β-enone 13 as a colorless pwer (one diastereomer): R$_f$=0.45 (hexanes-ether 80:20); $[\alpha]^{23}{}_D$−45.3 (c 1.18, CHCl$_3$); FTIR (film) 1676 cm$^{-1}$; $^1$H NMR (400 MHz, CDCl$_3$) δ7.44–7.29 (m, 5H0, 6.21 (dd, J=16.0 10.8 Hz, 1H) m 5.79 (d, J=10.6 Hz, 1H), 5.52 (dd, J=15.2, 7.0 Hz, 1H), 4.92 (d, J=11.0 Hz, 1H), 4.83 (d, J=11.0 Hz, 1H), 2.79 (m, 1H), 2.60 (m, 1H), 2.50–2.30 (m, 2H), 2.13 (m, 1H), 2.79 (m, 1H), 2.60 (m, 1H), 2.50–2.30 (m, 2H), 2.13 (m, 1H), 1.77 (m, 6H), 1.68–1.27 (m, 6H), 1.19 (m, 6H), 0.95 (d, J=6.9 Hz, 3H) $^{13}$C NMR (100 MHz, CDCl$_3$) δ197.3, 154.9, 148.8, 138.1, 135.9, 133.6, 128.3, 128.1, 127.7, 125.6, 125.1, 73.1, 41.5, 40.9, 36.8, 35,9, 35.5, 31.2, 26.5, 26.0, 19.4, 18.4, 18.3, 15.3, 11.7, EIMS 392 [M]$^+$, 301 [M−Bn]$^+$; HRMS calcd for [C$_{27}$H$_{36}$O$_2$]$^+$ 392.2715, found 392.2709.

EXAMPLE 9

Phenolic Ether 14

Diisopropylamine (0.045 mL, 0.321 mmol) in THF (2 mL) was cooled to 0° C. and treated dropwise with n-BuLi (0.124 mL, 2.59 M solution in hexanes, 0.321 mmol). The solution was stirred for 15 min and cooled to −78° C. In a separate flask α,β-enone 13 (0.0420 g, 0.107 mmol) was azeotropically dried with benzene (1 mL), dissolved in THF (1 mL), and added dropwise via cannula to the reaction mixture (residual 13 was washed in with an additional 0.5 mL of THF). The solution was stirred for 15 min and treated with tert-butyldimethylsilyl trifluoromethanesulfonate (0.098 mL, 0.428 mmol). The reaction mixture was stirred for 15 min at −78° C., then warmed to 0° C. for 15 min. After the mixture was recooled to −78° C., triethylamine (1 mL) was added, folllowed by NaHCO$_3$ (saturated aqueous, 1 mL), and the mixture was allowed to warm to 23° C. Water was added, and the aqueous layer was extracted three times with petroleum ether. The combined organic layers were dried over K$_2$CO$_3$ (anhydrous), filtered, and concentrated in vacuo. The residue was purified by flash chromatography (hexanes-ether-triethylamine 89:10:1) to afford 0.0565 g (100%) of the enol TBS ether of Compound 13 as a clear oil: R$_f$=0.47 (MeOH, reverse phase C$_{18}$ plate); $^1$H NMR (500 MHz, C$_6$D$_6$) δ7.43 (d, J=7.8 Hz, 2H), 7.19 (t, J=7.6 Hz, 2H), 7.09 (t, J=7.5 Hz, 1H), 6.38 (dd, J=15.0, 10:7 Hz, 1H), 5.95 (d, J=10.8 Hz, 1H), 5.63 (dd, J=15.1, 7.0 Hz, 1H), 4,98 (d, J=11.8, Hz), 4.70 (d, J=11.8 Hz, 1H), 2.78 (m, 1H), 2.55 (m, 1H), 2.19 (m, 2H), 1.97 (m, 1H), 1.85 (s, 3H), 1.75 (m, 1H), 1.68 (s, 3H), 1.67 (s, 3H), 1.61 (m, 2H), 1.33 (m, 2H), 1.21 (d, J=7.1 Hz, 3H), 1.03 (s, 9H), 0.89 (d, J=6.9 Hz, 3H), 0.22 (s, 3H), 0.19 (s, 3H).

A solution of the above enol ether of Compound 13 (0.0148 g, 0.0292 mmol) in methyl-cyclohexane (0.9 mL) was treated with activated manganese dioxide (Aldrich Co., dried by azeotroping with toluene, 0.025 g, 0.292 mmol) and heated to 70° C. with stirring for 16 h. The mixture was filtered through Celite, washed extensively with methylene chloride and the solvent was removed in vacuo, affording crude phenolic ether 14 as a clear oil: R$_f$=0.48 (hexanes-Et$_2$O 95:5); $^1$H NMR MHz, CDCl$_3$) δ7.34 (m, 5H), 6.73 (s, 1H), 6.15 (dd, J=15.2, 10.8 Hz, 1H), 5.82 (d, J=10.7 Hz, 1H), 5.60 (dd, J=15.2, 6.9 Hz, 1H), 5.07 (d, J=12.1 Hz, 1H), 4,77 (d, J=12.1 Hz, 1H), 2.94 (m, 1H), 2.65 (m, 1H), 2.61 (m, 1H), 2,21 (s, 3H), 1.81–1.72 (m, 2H), 1.77 (s, 3H), 1.74 (s, 3H), 1.66 (m, 1H), 1.37 (m, 1H), 1.17 (d, J=6.9 Hz, 3H), 1.00 (s, 9H), 0.88 (d, J=6.8 Hz, 3H), 0.14 (s, 3H), 0.08 (s, 3H).

EXAMPLE 10

Mesylate 15

Phenolic ether 14 was dissolved in THF (1.5 mL) and treated dropwise with tetrabutylammonium fluoride (0.060 mL, 1.0M solution in THF, 0.060 mmol). After the mixture stirred for 5 min, silica gel (0.5 mL) was added, and the mixture was concentrated in vacuo. The product absorbed on silica gel was purified by flash chromatography (hexanes-ether 95:5) to afford 0.0098 g (86% from 13) of the free phenol as a colorless powder: R$_f$=0.41 (hexanes-ether 80:20); [α]$^{23}$$_D$−47 (c 0.80, CHCl$_3$); FTIR (film) 3510 cm$_{-1}$; $^1$H NMR (400 MHz, CDCl$_3$) δ7.42 (m, 5H), 6.74 (s, 1H), 6.17 (dd, J=15.0, 10.8 Hz, 1H), 5.83 (d, J=10.8 Hz, 1H), 5.62 (dd, J=15.2, 6.7 Hz, 1H), 5.39 (s, 1H), 4.99 (d, J=11.4 Hz, 1H), 4.80 (d, J=11.4 Hz, 1H), 3.09 (m, 1H), 2.67 (m, 2H), 2.20 (s, 3H), 1.93–1.81 (m, 2H), 1.77 (s, 3H), 1.75 (s, 3H), 1.68 (m, 1H), 1.45 (m, 1H), 1.24 (d, J=6.9 Hz, 3H), 0.92 (d, J=6.7 Hz, 3H); $^{13}$C NMR (100 MHz, CDCl$_3$) δ145.2, 143.4, 137.3, 133.7, 133.0, 130.5, 128.8, 128.4, 127.9, 127.2, 125.6, 125.3, 121.7, 75.6, 42.6, 41.5, 28.0, 27.8, 26.0, 22.3, 19.9, 18.3, 15.3, 15.6; CIMS (NH$_3$) 408 [M+NH$_4$]$^+$; HRMA calcd for [C$_{27}$H$_{34}$O$_2$+NH$_4$]$^+$ 408.2903, found 408, 2910.

This phenol (0.0292 g, 0.0748 mmol) was azeotropically dried with benzene (1 mL), dissolved in CH$_2$Cl$_2$ (1.9 mL), and cooled to −30° C. This solution was treated dropwise with triethylamine (0.21 mL, 0.150 mmol), followed by methane sulfonyl chloride (0.009 mL, 0.112 mmol), and stirred for 15 min. NaHCO$_3$ (saturated aqueous, 1 mL) was added, and the mixture was warmed to 23° C. Water was added, and the aqueous layer was extracted three times with ether. The combined organic extracts were washed with brine, dried over MgSO$_4$ (anhydrous), filtered, and concentrated in vacuo. The residue was purified by flash chromatography (hexanes-ether 90:10) to afford 0.0337 g (96%) of mesylate 15: R$_f$=0.41 (hexanes-EtOAc 80:20); [α]$^{23}$$_D$−109 (c 0.97, CHCl$_3$); FTIR (film) 1368, 1170 cm$^{−1}$; $^1$H NMR (500 MHz, CDCl$_3$) δ7.43–7.35 (m, 5H), 6.86 (s, 1H), 6.13 (dd, J=15.1, 10.8 Hz, 1H), 5.82 (d, J=10.7, Hz, 1H). 5.58 (dd, J=15.1, 7.0 Hz, 1H), 5.02 (d, J=11.1 Hz, 1H, 4.91 (d, J=11.1 Hz, 1H), 3.10 (s, 3H), 3.06 (m, 1H), 2.69 (m, 1H), 2.61 (sex, J=6.4 Hz, 1H), 2.36 (s, 3H), 1.80 (m, 2H), 1.77 (s, 3H), 1.73 (s, 3H), 1.71 (m, 1H), 1.46 (m, 1H), 1.20 (d, J=6.9 Hz, 3H), 0.91 (d, J=6.9 Hz, 3H); $^3$C NMR (100 MHz, CDCl$_3$) δ148.2, 140.6, 138.8, 136.9, 136.7, 135.9, 133.5, 130.3, 128.6, 128.2, 128.1, 127.9, 126.1, 125.1, 75.7, 42.6, 41.6, 39.3, 27.7, 27.0, 26.0, 22.3, 19.3, 18.3, 17.0, 16.5; FABMS (Na) 491 [M+Na]$^+$, 359 [M−C$_8$H$_{13}$]$^+$; HRMS calcd for [C$_{28}$H$_{36}$O$_4$S+Na]$^+$ 491.2232, found 491.2222.

EXAMPLE 11

Tricycle 16

A solution of Mesylate 15 (0.0337 g, 0.0719 mmol) in CH$_2$Cl$_2$ (7.2 mL) was cooled to −78° C. and treated dropwise with methane sulfonic acid (0.023 mL, 0.360 mmol). The solution was warmed to −50° C. and stirred for 10 h, and then triethylamine (0.150 mL) was added. The mixture was warmed to 23° C., filtered through a small plug of silica gel (hexanes-EtOAc 80:20), and concentrated in vacuo to afford 0.0338 g (100%) of tricycle 16 as a clear oil: R$_f$=0.41 (hexanes-EtOAc 80:20); [α]$^{23}$$_D$−109 (c 0.92, CHCl$_3$); FTIR (film) 1367, 1177 cm$^{−1}$; $^1$H NMR (500 MHz, CDCl$_3$) δ7.40 (m, 5H), 5.11 (dt, J=9.2, 1.2 Hz, 1H), 4.95 (d, J=11.0 Hz, 1H), 4.84 (d, J=11.0 Hz, 1H), 3.63 (br d, J=9.1 Hz, 1H), 3.36 (m, 1H), 3.06 (s, 3H), 2.21 (m, 1H), 2.19 (s, 3H), 2.10 (td, J=10.4, 4.3 Hz, 1H), 1.95 (m, 1H), 1.75 (s, 3H), 1.70 (s, 3H), 1.69–1.50 (m, 4H), 1.24 (d, J=7.1 Hz, 3H), 1.11 (tt, J=9.8, 1.9 Hz, 1H), 1.05 (d, J=5.9 Hz, 3H); $^{13}$C NMR (100 MHz, CDCl$_3$) δ146.0, 40.6, 137.6, 137.1, 135.5, 135.1, 130.9, 129.9, 129.0, 128.7, 128.3, 127.9, 75.8, 42.4, 39.3, 39.1, 35.8, 30.1, 29.5, 27.6, 27.5, 25.8, 23.3, 21.0, 17.7, 12.8; EIMS 468 [M]$^+$; HRMS calcd for C$_{28}$H$_{36}$O$_4$S]$^+$ 468.2334, found 468.2333.

EXAMPLE 12

Phenol 17

Tricycle 16 (0.0124 g, 0.0265 mmol) was azeotropically dried with benzene (0.5 mL), dissolved in THF (0.25 mL), and cooled to 0° C. This solution was treated dropwise with MeMgBr (0.018 mL, 3.0 M solution in ether, 0.053 mmol) and stirred for 18 h. NH$_4$Cl (saturated aqueous) was added and the aqueous layer was extracted three times with ether. The combined organic layers were dried over MgSO$_4$ (anhydrous), filtered, and concentrated in vacuo. The residue was purified by flash chromatography (hexanes-ether 95:5) to afford 0.0100 g (97%) of tricyclic phenol 17 (25:1 mixture of diastereomers) as a clear oil: R$_f$= 0.55 (hexanes-EtOAc 80:20); [α]$^{23}$$_D$-104 (c 1.00, CHCl$_3$); FTIR (film) 3529, 1451 cm$^{-1}$; $^1$H NMR (400 MHz, CDCl$_3$) δ7.43 (m, 5H), 5.49, (s, 1H), 5.14 (dt, J=9.2, 1.2 Hz, 1H), 4.89 (d, J=11.2 Hz, 1H), 4.83 (d, J=11.2 Hz, 1H), 3.63 (dt, J=9.0, 3.4 Hz, 1H), 3.38 (m, 1H), 2.21 (m, 1H), 2.12 (dt, J=10.5, 4.8 Hz, 1H), 2.05 (s, 3H), 2.00 (m, 1H), 1.76 (d, J=0.9 Hz, 3H) 1.69 (s, 3H), 1.68–1.50 (m, 4H), 1.30 (d, J=7.1 Hz, 3H), 1.13 (m, 1H), 1.05 (d, J=6.1 Hz, 3H); $^{13}$C NMR (100 MHz, CDCl$_3$) δ145.0, 141.9, 137.4, 134.8, 132.9, 130.0, 129.8, 129.3, 128.8, 128.4, 127.9, 120.5, 75.9, 42.0, 39.5, 35.6, 30.6, 29.9, 27.8, 27.6, 25.8, 23.1, 21.0, 17.8, 10.8; EIMS 390 [M]$^+$, 299 [M−Bn]$^+$; HRMS calcd for [C$_{27}$H$_{34}$O$_2$]$^+$ 390.2559, found 390.2563.

EXAMPLE 13

Pseudopterosin Aglycone 3

Phenol 17 (0.0148 g, 0.0379 mmol) was azeotropically dried with benzene (0.5 mL), dissolved in CH$_2$Cl$_2$ (0.5 mL), and cooled to 0° C. The solution was treated dropwise with BBr$_3$ (0.00379 mmol) in CH$_2$Cl$_2$ (0.100 mL). After 4 min. NaHCO$_3$ (saturated aqueous, 1 mL) was added, and the mixture was allowed to warm to room temperature. Water was added, and the aqueous layer was extracted three times with CH$_2$Cl$_2$.The combined organic extracts were dried over Na$_2$SO$_4$ (anhydrous), filtered, and concentrated in vacuo. The residue was purified by flash chromatography (hexanes-EtOAc 90:10) to afford 0.0094 g (83%) of pseudopterosin aglycone (3) as an oil: R$_f$=0.28 (hexanes-EtOAc 80:20); [α]$^{23}$$_D$-95 (c 0.94, CHCl$_3$); FTIR (film) 3449, 1448 cm$^{-1}$; $^1$H NMR (500 MHz, CDCl$_3$) δ5.11 (dt, J=9.2, 1.4 Hz, 1H), 5.03 (br s, 1H), 4.82 (br s, 1H), 3,58 (m, 1H), 3.22 (m, 1H), 2.17 (m, 2H), 2.03 (s, 3H), 2.02 (m, 1H), 1.75 (d, J=1.1 Hz, 3H), 1.67 (s, 3H), 1.65–1.46 (m, 4H), 1.25 (d, J=7.0 Hz, 3H), 1.08 (m, 1H), 10.4 (d, J=6.3 Hz, 3H); $^{13}$C NMR (100 MHz, CDCl$_3$) δ139.9, 139.7, 130.3, 130.2, 129.9, 129.7, 125.9, 119.8, 43., 39.5, 35.4, 31.0, 30.0, 28.3, 27.4, 25.7, 23.1, 21.0, 17.7, 10.9; EIMS 300 [M]$^+$; HRMS calcd for [C$_{20}$H$_{28}$O$_2$]$^+$ 300.2089. Found 300.2096.

EXAMPLE 14

Enol Ether 21

Diisopropyl amine (0.34 mL, 2.40 mmol) in THF (10 mL) was cooled to 0° C. and treated dropwise with n-BuLi (0.92 mL, 2.61 M solution in hexanes, 2.40 mmol). The solution was stirred for 15 min and cooled to −78° C. In a separate flask, dihydrocarvone$^{20}$ (0.2434 g., 1.599 mmol) was azeotropically dried with benzene (1 ml), dissolved in THF (1 mL), and added dropwise via cannula to the reaction mixture (residual dihydrocarvoce was washed in with an additional 0.5 mL of THF). The solution was stirred for 15 min. And treated with tert-butyl-dimethylsilyl trifluoromethane-sulfonate (0.73 mL, 3.20 mmol). The reaction mixture was stirred for 15 min at −78° C. and then warmed to 0° C. for 15 min. Triethylamine (2 mL) was added, followed by NaHCO$_3$ (saturated aqueous, 5 mL:), and the mixture was allowed to warm to 23° C. Water was added and the aqueous layer was extracted three times with petroleum ether. The combined organic layers were dried over K$_2$CO$_3$ (anhydrous), filtered, and concentrated in vacuo. The residue was purified by flash chromatography (hexanes-Et$_2$O-triethylamine 89:10:1) to afford 0.423 g (99%) of enol ether 21 as a clear oil: R$_f$=0.73 (hexanes-ether 90:10); [α]$^{23}$$_D$+62 (c 0.95, CHCl$_3$); $^1$H NMR (400 MHz, CDCl$_3$) δ5.56 (m, 1H), 4.76 (d, J=3.3 Hz, 1H), 2.16 (m, 1H), 2.00 (m, 2H), 1.72 (s, 3H), 1.60 (sept, J=6.6 Hz, 1H), 0.94 (s, 9H), 0.86 (m, 6H), 0.17 (s, 3H), 0.16 (s, 3H); $^{13}$C NMR (100 MHz, CDCl$_3$) δ149.8, 132,2, 123.7, 105.5, 40.5, 31.7, 26.4, 25.9, 25.8, 20.0, 19.9, 18.3, 17.7, −2.5, −4.3, −4.5; CIMS (NH$_3$) 284 [M+NH$_4$]$^+$, 267 [M+H]$^+$; HRMS calcd for [C$_{16}$H$_{30}$OSi+H]$^+$ 267.2144, found 267.2149.

EXAMPLE 15

TBS Ether 22

A solution of the enol TBS ether of dihydrocarvone 21 (0.0623 g, 0.234 mmol) in methylcyclohexane (5 mL) was treated with activated manganese dioxide (azeotroped from toluene, 0.200 g, 2.38 mmol) and heated to 70° C. After 36 h., the mixture was filtered through Celite and washed extensively with CH$_2$Cl$_2$. The solvent was removed in vacuo, and the residue was filtered through a short plug of silica gel (hexanes-Et$_2$O 90:10) affording 0.0521 g (84%) of ether 22 as a clear oil: R$_f$=0.38 (MeOH, reverse phase C$_{18}$ plate); $^1$H NMR (400 MHz, CDCl$_3$) δ7.04 (d, J=7.6 Hz, 1H), 6.73 (dd, J=7.7, 1.7 Hz, 1H), 6.63 (d, J=1.6 Hz, 1H), 2.81 (SEPT, J=6.9 Hz, 1H), 2.17 (s, 3H), 1.21 (D, J=6.9 Hz, 6H), 1.02 (s, 9H), 0.22 (s, 6H); $^{13}$C NMR (100 MHz, CDCl$_3$) δ153.8, 147.7, 130.7, 126.1, 119.0, 116.8, 33.7, 25.9, 24.1, 18.3, 16.4, −4.1; CIMS (NH$_3$) 282 [N+NH$_4$]$^+$, 265 [M+H]$^+$; HRMS calcd for [C$_{16}$H$_{28}$OSi+NH$_4$]$^+$282.2253, found 282.2251.

EXAMPLE 16

Anisoate 24

A solution of diene 23$^{21}$ (0.0490 g, 0.190 mmol) in methylcyclo-hexane (2 mL) was treated with manganese dioxide (azeotroped from toluene, 0.207 g, 2.46 mmol), heated to 70° C., and stirred for 36 h. The reaction mixture was filtered through Celite and washed extensively with CH$_2$Cl$_2$. The solvent was removed in vacuo to afford 0.0403 g (83%) of anisoate 24 as a clear oil: R$_f$=0.30 (hexanes-Et$_2$), 80:20); FTIR (film) 1712, 1261 cm$^{-1}$, $^1$H NMR (400 MHz, CDCl$_3$) δ8.02 (d, J=9.0 Hz, 2H), 7.34 (d, J=8.0 Hz, 2H), 7.19 (d, J=7.9 Hz, 2H), 6.91 (d, J=9.0 Hz, 2H), 5.30 (s, 3H), 3.85 (s, 3H), 2.36 (s, 3H); $^{13}$C NMR (100 MHz, CDCl$_3$) δ166.3, 163.5, 138.0, 133.4, 131.8, 129.3, 122.7, 113.6, 66.4, 55.5, 21.3; CIMS 256 [M]$^+$; HRMS calcd for [C$_{16}$H$_{16}$O$_3$$^+$]$^+$ 256.1100, found 256.1099.

EXAMPLE 17

4-Methoxyphenyl Ether 26

A solution of Diene 25$^{21}$ (0.0509 g, 0.208 mmol) in methylcyclohexane (2 mL) was treated with manganese dioxide ((azeotroped from toluene, 0.228 g., 2.71 mmol), heated to 70° C., and stirred for 36 h. The reaction mixture was filtered through Celite and washed extensively with CH$_2$Cl$_2$. The solvent was removed in vacuo, and the residue was purified by silica gel chromatography (hexanes-Et$_2$O 80:20); FTIR (film) 1509, 1232 cm$^{-1}$; $^1$H NMR (400 MHz, CDCl$_3$) δ7.19 (d, J=8.0 Hz, 2H), 7.14 (d, J=8.0 Hz, 2H), 6.84 (m, 4H), 4.11 t, J=7.2 Hz, 2H), 3.77 (s, 3H), 3.05 (t, J=7.2 Hz, 2H), 2.35 (s, 3H),.; $^{13}$C NMR (100 MHz, CDCl$_3$) δ153.9 153.0, 136.0, 135.3, 129.2, 128.9, 115.6, 114.7, 69.6, 55.8, 35.8, 21.1; EIMS 242 [M]$^+$; HRMS calcd for [C$_{16}$H$_{18}$O$_2$$^+$]$^+$ 242.1307, found 242.1302.

REFERENCES

The following references have been cited herein as background information related to this application. To the extent necessary for a complete understanding of the invention, the disclosures of these publications are hereby incorporated herein by reference:

(1) (a) Look, S. A.; Fenical, W.; Matsumoto, G.; Clardy, J. *J. Org. Chem.* 1986, 51, 5140–5145; (b) Fenical, W. *J. Nat. Prod.* 1987, 50, 1001–1008 (c) Look, S. A.; Fenical W. *Tetrahedron*987, 43, 3363–3370.

(2) Look, S. A.; Fenical, W.; Jacobs, R. S.; Clardy, J. *Proc. Natl. Acad. Sci USA.* 1986, 83, 6238–6240

(3) Personal communication from Professor William Fenical whom we thank for his information and for generously providing samples of naturally derived pseudopterosins A and E.

(4) Rouhi, A. M. *Chem. Eng. News* 1995, November 20, 42044.

(5) Broka, C. A.; Chan, S.; Peterson, B. *J. Org. Chem.* 1988, 53, 1584– 1586.

(6) (a) Corey, E. J.; Carpino, P. *J. Am. Chem. Soc.*1989, 111, 5472–5474; (b) Corey, E. J.; Carpino, P. *Tetrahedron Lett.* 1990, 31, 3857–3858.

(7) (a) McCombie, S. W.; Co, B; Lin, S. I.; Ganguly, A. K.; McPhail, A. T. *Tetrahedron Lett.* 1991, 32, 2083–2086; (b) McCombie, S. W.; Ortiz, C; Cox, B.; Ganguly, A. K. *Synlett* 1993, 541–547.

(8) (a) Buszek, K. R. *Tetrahedron Lett.* 1995, 36, 9125–9128; (b) Buszek, K. R.; Bixby, D. L. *Tetrahedron Lett.* 1995, 36, 9129–9132.

(9) Gill. S.; Kocienski, P.; Kohler, A.; Pontiroli, A.; Qun, L. *J. Chem. Soc., Chem. Commun.* 1996, 1743–1744.

(10) (a) Majdalani, A.; Schmalz, H. G. *Tetrahedron Lett.* 1997, 38, 4545–4548; (b) Majdalani, A.; Schmalz, H. G. Synlett. 1997, 1303–1305; (c) Kato, N.; Zhang, C. S.; Matsui, T.; Iwabachi, H.; Mori, A.; Ballio, A.; Sassa, T., J. *Chem. Soc., Perkin Trans.* 1 1998, 2475.

(11) (a) Brow, H. C.; Pfaffenberger, C. D. *J. Am. Chem. Soc.* 1967, 89, 5475–5477; (b) Brown, H. C.; Negishi, E. I. *Tetrahedron* 1977, 33, 2331–2357.

(12) Stevens, R. V.; Chapman, K. T.; Stubbs, C. A.; Tam, W. W.; Albizati, K. F. *Tetrahedron Lett.* 1982, 23, 4647–4650.

(13) Aneli, P. A.; Banfi, S.; Montanari, F.; Quici, S. *J. Org. Chem.* 1989, 54, 2970–2972.

(14) (a) Vedejs, E.; Fang, H. W. *J. Org Chem.* 1984, 49, 210–212; (b) Cristau, H.-J.; Ribeill, Y. *Synthesis* 1988, 911, 912.

(15) The α,β-enone 11 was prepared by Swern oxidation of 1-benzyloxy-3-methylbut-3-ene-2-ol, see: Terao, S.; Shiraishi, M.; Kato, K. *Synthesis* 1979, 467–468.

(16) For some examples of Mukaiyama-type Michael Reactions see: (a) Narasaka, K.; Soai, K.; Aikawa, Y.; Mukaiyama, T. *Bull Chem. Soc. Jpn.* 1976, 49, 779–783; (b) Heathcock, C. H.; Norman, M. H.; Uehling, D. E. *J. Am. Chem. Soc.* 1985, 107, 2797–2799; (c) Ranu, B. C.; Saha, M.; Bhar S. *J. Chem. Soc., Perkin Trans.* 1 1994, 2197–2199 and references therein

(17) See (a) Mashraqui, S.; Keehn, P. *Synth. Commun.* 1982, 12, 637–645; (b) Sodeoka, M.; Satoh, S.; Shibasaki, M. *J. Am. Chem. Soc.* 1988, 110, 4823–4824.

(18) Problems with these reagents included disilylation of the starting material and interfering processes involving the diene appendage.

(19) See Corey, E. J.; Sauers, C. K. *J. Am. Chem. Soc.* 1957, 79, 248.

(20) Prepared by Mr. Steven N. Goodman, of the Harvard-Corey group, according to the procedure found in: Deslongchamps, P.; Belanger, A.; Berney, D. J. F.; Borschberg, H.-J.; Brosseau, R.; Boutheau, A.; Durand, R.; Katayama, H.; Lapalme, R.; Leture, D. M.; Liao, D.-C.; MacLachlan, F. N.; Maffraud, J.-P.; Marazza, F.; Martino, R.; Moreau, C.; Ruest, L.; Saint-Laurent, L.; Santonge, R; Soucy, P., *Cam J. Chem.* 1990, 68, 127–152.

(21) Corey, E. J.; Guzman-Perez, A.; Noe, M. C. *J. Am. Chem. Soc.* 1995, 117, 10805–10816.

The present invention has been described in detail, including the preferred embodiments thereof. However, it will be appreciated that those skilled in the art, upon consideration of the present disclosure, may make modifications and/or improvements on this invention and still be within the scope and spirit of this invention as set forth in the following claims.

What is claimed is:

1. A process for the synthesis of the pseudopterosin aglycone of formula 3:

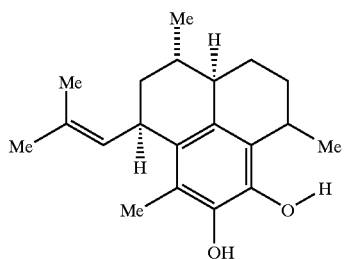

3 which process comprises the following steps:

(a) oxidation of a diol mixture of Formula 4:

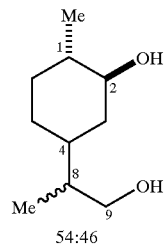

4 to form a diastereomeric mixture of hydroxy ketones of Formula 5:

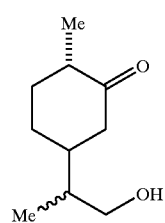

5

(b) treating the ketone mixture 5 with isopropenyl acetate and PS lipase, from *Pseudomonas cepacia*, as a catalyst to achieve the selective acetylation of the (8S)-hydroxy ketone, which was separated from the desired (8R)-alcohol of Formula 6 by flash chromatography:

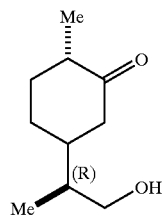

6

(c) oxidation of the alcohol of Formula 6 to form a keto aldehyde of Formula 7:

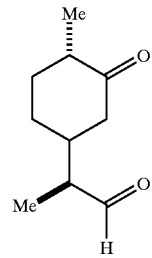

7

(d) olefination of the keto aldehyde of Formula 7 with a ylide of Formula 8, to form a keto-diene of Formula 9:

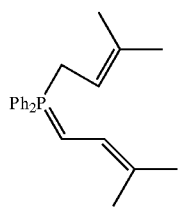

8

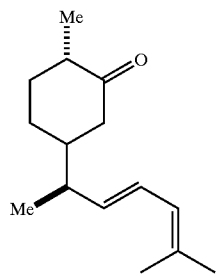

9

(e) reduction of the keto-diene of Formula 9 to form an enol silyl ether of Formula 10:

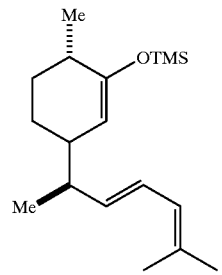

10

(f) combining the enol silyl ether of Formula 10 with an α,β-enone of Formula 11, to produce a diketone of Formula 12:

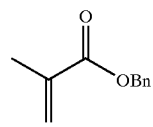

11

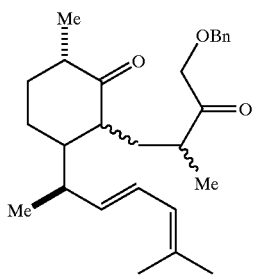

12

(g) aldol cyclizaton of the diketone of Formula 12 to provide a β-hydroxy ketone which was then dehydrated to form an an α,β-enone of

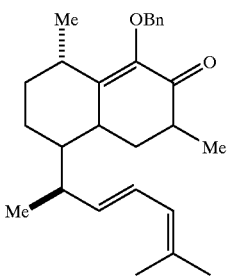

13

(h) forming the enol tert-butyldimethylsilyl ether of Formula 13 by deprotonation and silylation; then aromatizing the enol tert-butyldimethylsilyl ether with $MnO_2$ to provide an aromatic hydronaphthalene of Formula 14, followed by reaction with $CH_3$—$SO_2Cl$—$Et_3N$ to provide a mesylate of Formula 15:

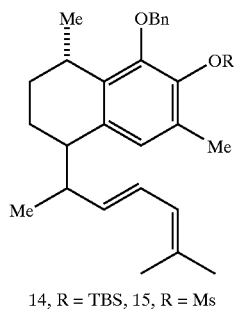

14, R = TBS, 15, R = Ms (i) diasteroselective cationic cyclization of the mesylate of Formula 15 to provide a tricyclic compound of Formula 16:

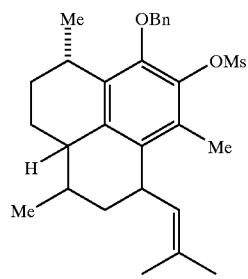

16

(j) reaction of the tricyclic compound of Formula 16 with MeMgBr to produce a monophenol of Formula 17, followed by debenzylation to give the pseudopterosin aglycone of Formula 3:

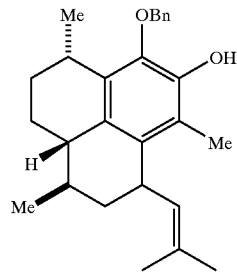

17

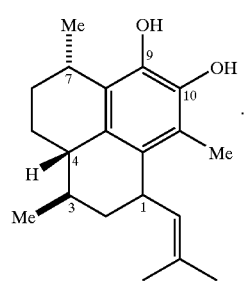

3

2. A method of separating the R and S diastereomers of Formula 5:

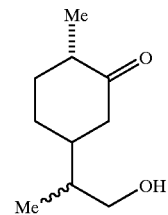

5 comprising treating the mixture of diastereomers with PS lipase, a lipase from *Pseudomonas cepacia,* and isopropenyl acetate, followed by chromatographic separation of (1S, 4S, 8R)-(+)-meth-2-one-9-ol from 8S acetate.

3. A process for the aromatic annulation of the compounds of Formulae 9 through 14, comprising the following steps:

(a) reduction of the keto-diene of Formula 9 to form an enol silyl ether of Formula 10:

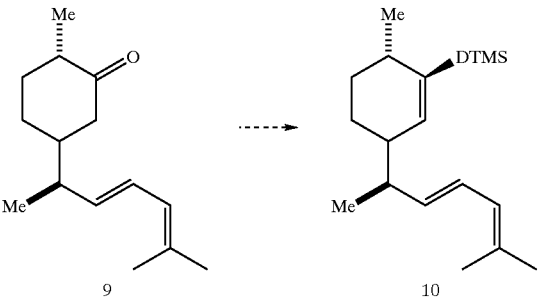

(b) combining the enol silyl ether of Formula 10 with an α,β-enone of Formula 11, to produce a diketone of Formula 12:

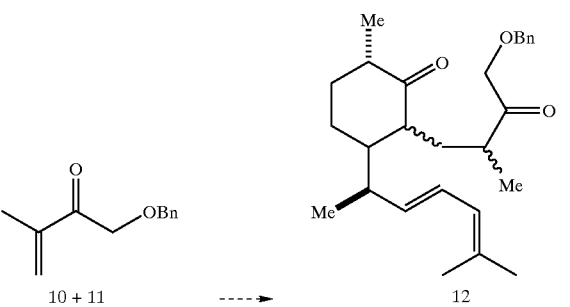

(c) aldol cyclizaton of the diketone of Formula 12 to provide αβ-hydroxy tone which was then dehydrated to form an α,β-enone of Formula 13:

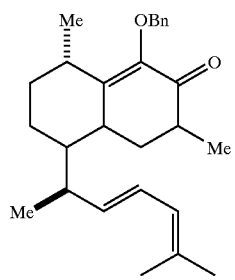

(d) forming the enol tert-butyldimethylsilyl ether of Formula 13 by deprotonation and silylation; then aromatizing the enol tert-butyldimethylsilyl ether with MnO$_2$ to provide an aromatic hydronaphthalene of Formula 14:

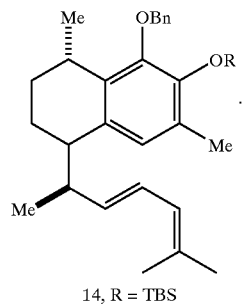

4. A process for the stereoselective cyctization of the compound of Formula 15 to yield the compound of Formula 16, comprising the treatment of 15 with methanesulfonic acid:

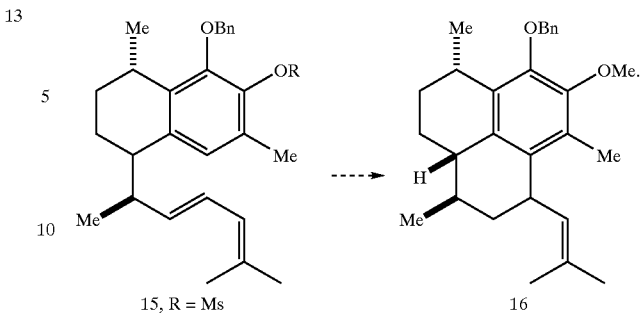

5. A process for the stereoselective cyclization of the compound of Formula 14 to yield the compound of Formula 18, comprising treatment of 14 with methanesulfonic acid:

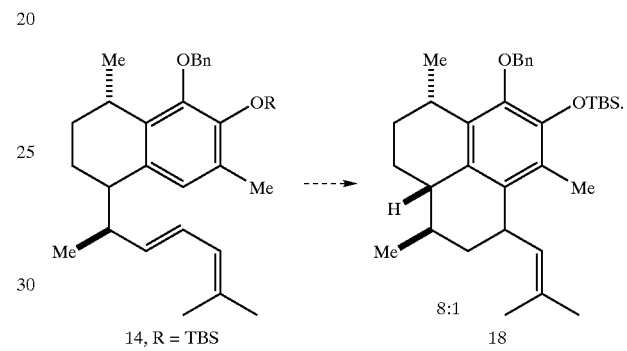

* * * * *